United States Patent [19]

Cywinski

[11] 4,365,080

[45] Dec. 21, 1982

[54] PRODUCTION OF DIMETHYL ESTERS

[75] Inventor: Norbert F. Cywinski, Odessa, Tex.

[73] Assignee: El Paso Products Company, Odessa, Tex.

[21] Appl. No.: 265,632

[22] Filed: May 20, 1981

[51] Int. Cl.³ .............................................. C07C 67/08
[52] U.S. Cl. .................................... 560/204; 203/14; 203/15; 203/16; 203/38; 203/39; 203/43; 203/66
[58] Field of Search .................... 560/204; 203/14, 15, 203/16, 38, 43, 66, 39

[56] References Cited

U.S. PATENT DOCUMENTS

| 3,574,706 | 4/1971 | Cevidalli et al. | 560/204 |
| 3,734,951 | 5/1973 | Suter et al. | 560/204 |
| 3,859,335 | 1/1975 | Schindlbauer et al. | 560/204 |
| 3,991,100 | 11/1976 | Hochberg | 560/204 |
| 4,105,856 | 8/1978 | Newton | 560/204 |

*Primary Examiner*—Natalie Trousof
*Assistant Examiner*—Vera C. Clarke
*Attorney, Agent, or Firm*—Depaoli & O'Brien

[57] ABSTRACT

This invention provides an improved process for the separation and recovery of byproducts associated with the isolation of $C_4$–$C_6$ dicarboxylic acids contained in a waste byproduct stream derived from an adipic acid manufacturing operation involving nitric acid oxidation of a cyclohexanone/cyclohexanol feedstream.

The main byproducts which are recovered are high purity dimethyl succinate, dimethyl glutarate and dimethyl adipate.

12 Claims, 1 Drawing Figure

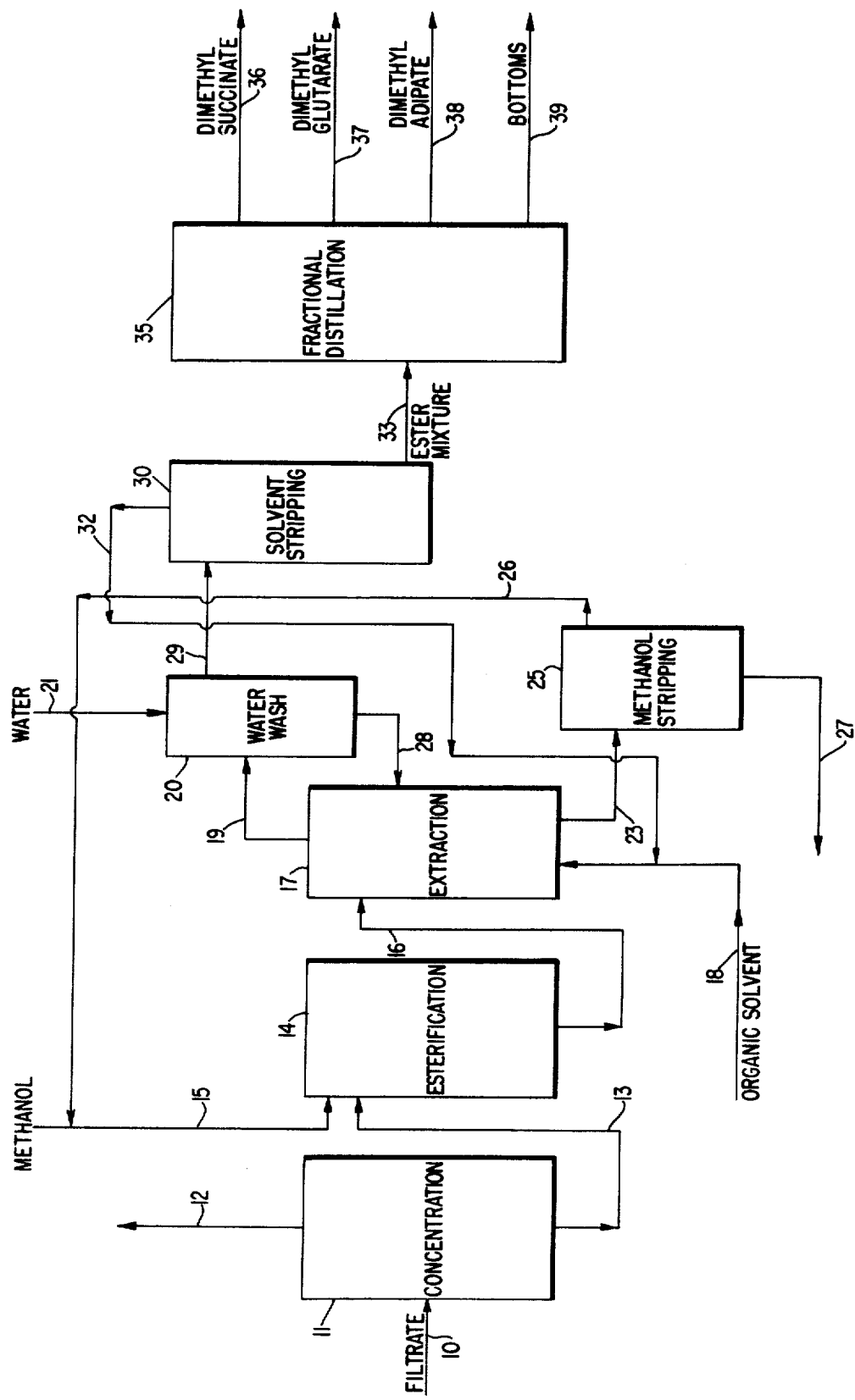

4,365,080

PRODUCTION OF DIMETHYL ESTERS

BACKGROUND OF THE INVENTION

Adipic acid is an important intermediate for the production of nylon. Commercial methods for producing dicarboxylic acids generally involve oxidizing naphthenes, cycloaliphatic ketones or cycloaliphatic alcohols with nitric acid in the presence of metal oxidation catalysts.

In the case of adipic acid, specific feed materials such as cyclohexane, cyclohexanol and/or cyclohexanone in admixture with nitric acid are heated at about 40°–140° C. in the presence of a catalyst. The resultant oxidation reaction product comprises adipic acid together with small amounts of monocarboxylic acids and dicarboxylic acids and other organic components in admixture with nitric acid and catalyst components. A substantial quantity of the adipic acid product is recovered by cooling the solution and filtering off the crystallized adipic acid. Oxidation methods of adipic acid production are described in U.S. Pat. Nos. 2,439,513; 2,557,281; 2,719,566; 2,840,607; 2,971,010; 3,338,959; and references cited therein.

In a process involving nitric acid oxidation of cyclohexanol and/or cyclohexanone, economically significant amounts of succinic acid and glutaric acid are formed as byproducts in admixture with the adipic acid. After the major portion of the adipic acid is separated by crystallization and filtration, the filtrate mother liquor contains some adipic acid, as well as succinic acid, glutaric acid, nitric acid and metal catalyst values.

Usually this filtrate has been treated as a waste stream. Because of environmental and economic considerations, there has been continuing research effort to develop methods for recovering the valuable and reusable organic and inorganic components of the said filtrate waste byproduct stream.

U.S. Pat. No. 3,726,888 describes a process for the separation and recovery of the components contained in the filtrate waste byproduct stream of an adipic acid manufacturing plant. The filtrate stream comprises a mixture of adipic acid, glutaric acid, succinic acid, metal catalyst values and nitric acid. The separation and recovery process involves contacting the filtrate with alkanol, and extracting with a water-immiscible organic solvent to provide an organic phase containing the formed esters, and to provide an aqueous phase containing the nitric acid and metal catalyst values. Each of the phases is fractionated to separate the mixtures into useful components.

U.S. Pat. Nos. 4,076,948 and 4,082,788 describe processing improvements which are adapted to overcome some of the difficulties characteristic of the byproduct separation and recovery technology disclosed in the above recited U.S. Pat. No. 3,726,888. There remains a need for further improvements in this kind of byproduct separation and recovery technology.

Accordingly, it is an object of this invention to provide an improved process for the recovery of organic acids from dilute aqueous solutions.

It is a further object of this invention to provide an improved process for the separation and recovery of dicarboxylic acids and other valuable components contained in a filtrate byproduct stream derived from an adipic acid manufacturing operation involving nitric acid oxidation of cyclohexanol and/or cyclohexanone.

Other objects and advantages of the present invention shall become apparent from the accompanying description and exemplary data.

DESCRIPTION OF THE INVENTION

One or more objects of the present invention are accomplished by the provision of an improved process for producing methyl esters of $C_4$–$C_6$ carboxylic acid components contained in an aqueous filtrate, which filtrate is a waste byproduct stream derived from the production of adipic acid by nitric acid oxidation of cyclohexanone/cyclohexanol, the improvement which comprises the steps of (1) concentrating the volume of the aqueous filtrate medium by the partial removal of water and the volatile components which co-distill with water to provide a concentrate solution; (2) admixing the concentrate solution with methanol, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; and (4) separating the immiscible organic solvent phase and aqueous phase.

In another embodiment, this invention provides an improved method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the organic solvent phase and washing the said phase with water to reduce the content of methanol and residual nitric acid; and (5) recovering the solvent phase which contains dimethyl succinate, dimethyl glutarate and dimethyl adipate components.

In a further embodiment this invention contemplates an improved method for producing dimethyl esters and for providing for the recovery of a nitric acid solution containing metal catalyst values, wherein the said method involves the production of dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the immiscible organic solvent phase and aqueous phase; (5) fractionally distilling the organic solvent phase to recover a refined mixed dimethyl ester fraction; and (6) concentrating the aqueous phase by distillation to provide a residual aqueous solution containing nitric acid and metal catalyst values.

As noted previously, in the oxidation of cyclohexanol and/or cyclohexanone with nitric acid in the presence of a metal oxidation catalyst, the resulting oxidation product solution is processed for recovery of the bulk of the desired adipic acid by crystallization and filtration. The acidic mother liquor (i.e., the aqueous filtrate byproduct stream) contains quantities of monobasic and dibasic carboxylic acids as well as nitric acid and metal catalyst values. These filtrate components are sufficiently valuable to invite the application of recovery procedures.

A typical filtrate byproduct stream nominally corresponds to the following weight percent composition:

| Component | Amount |
| --- | --- |
| Succinic acid | 3–10% |
| Glutaric acid | 8–35% |
| Adipic acid | 3–6% |
| Nitric acid | 6–20% |
| Catalyst | 1–3% |
| Water | Balance |

The catalyst values contained in the filtrate are those which are conventionally employed in cyclohexanol/cyclohexanone oxidation procedures, such as copper, vanadium, and the like.

An important aspect of the present invention improved process is the step (1) concentration of the volume of the aqueous filtrate medium by the removal of water and nitric acid, and other volatile components which co-distill with water. The volatile components which co-distill with the water and nitric acid include butyric acid, valeric acid and caproic acid.

Several advantages derive from the step (1) concentration of the aqueous filtrate byproduct stream.

First, the reduced volume of the filtrate medium permits the use of smaller capacity equipment for the subsequent esterification and extraction steps of the process.

Second, the reduced proportion of water in the filtrate concentration solution causes a favorable equilibrium shift toward ester formation in the step (2) esterification reaction.

Third, the removal of monobasic acids during the step (1) concentration of the filtrate byproduct stream facilitates the production and recovery of dimethyl esters having improved color and odor specifications.

Fourth, the removal of nitric acid during the step (1) concentration of the filtrate byproduct stream has the important advantage of reducing the level of methyl nitrite and methyl nitrate byproduct formation during the step (2) esterification. The formation of these byproducts is primarily a function of the nitric acid concentration. These byproducts are undesirable because they cause the loss of both methanol and nitric acid. Further, these byproducts tend to be unstable and represent a potential explosion hazard. They must be purged periodically from the process system.

Fifth, the recovery of nitric acid during the step (1) concentration phase permits a highly efficient recycle of the said nitric acid to the cyclohexanol/cyclohexanone oxidation system.

With reference to step (2) of the invention process, a unique feature of the esterification reaction is the rate efficiency with which equilibrium is achieved between the esterified and unesterified dicarboxylic acid components, even in the presence of a highly dilute aqueous nitric acid solution. The efficiency of the step (2) esterification reaction is attributable to a combination of determining factors, such as an elevated reaction temperature, a high proportion of methanol relative to a low proportion of water, the absence of interfering byproduct components (e.g., monocarboxylic acids), and the like.

The step (2) esterification reaction time on the average will vary in the range between about 5–25 minutes, depending on the temperature maintained in the esterification zone.

In a similar manner, the combination of delimiting parameters of the step (3) extraction stage of the invention process provides technical advantages. Hence, an extraction temperature in the range between about 40° C.–90° C. has the beneficial effect of accelerating the additional conversion of free carboxylic acids to methyl ester derivatives. Substantially complete transfer of dimethyl esters is achieved during the step (3) extraction period. This efficient extraction of dimethyl esters by the organic solvent is readily accomplished within a phase contact period between about 2–20 minutes.

The quantity of water-immiscible organic solvent employed in the step (3) extraction stage of the invention process usually will vary in the range between about 0.5–2 volumes per volume of esterification medium being extracted, and on the average will approximate a volume ratio of 1:1.

A preferred type of water-immiscible organic solvent is one selected from aromatic hydrocarbons, halogenated aliphatic hydrocarbons and halogenated aromatic hydrocarbons. Particularly preferred species include benzene, toluene, xylene, ethylbenzene, chloroform, o-dichlorobenzene, and the like.

Because of the elevated temperature up to 90° C. employed during the esterification and extraction steps of the invention process, equipment is employed which is adapted for 15–200 psi reaction systems. The invention process can be conducted either batchwise or continuously.

At the end of the step (3) extraction period, the immiscible organic solvent and aqueous phases are separated and individually recovered for subsequent manipulative procedures.

In a particularly preferred embodiment, the organic solvent phase is contacted with wash water in a manner sufficient to remove substantially all of the methanol and residual nitric acid components present in the organic solvent phase, and to reduce the free carboxylic acids and monomethyl esters of dicarboxylic acids content of the organic solvent phase. The water washing step facilitates the subsequent recovery of high quality organic byproducts.

The said organic solvent phase can be distilled to strip the solvent medium, and yield a refined mixed dimethyl ester fraction. The said ester mixture can be employed directly to prepare high molecular weight esters applicable as plasticizers for polyvinyl chlorides. Alternatively, the ester mixture can be further fractionated to yield pure dimethyl succinate, dimethyl glutarate and dimethyl adipate, respectively. If desired, the dimethyl esters can be hydrolyzed to the corresponding high purity acids.

With respect to the aqueous phase which is separated and recovered after the step (3) extraction operation, preferably the said aqueous phase is subjected to concentration in vacuo to remove the dissolved methanol content and to provide a residual aqueous solution containing nitric acid and copper/vanadium type metal values. The said residual aqueous solution is suitable for recycle to the cyclohexanone/cyclohexanol oxidation system.

The practice of the present invention as a continuous process can be better understood by reference to the accompanying drawing which is illustrated as a flow diagram.

In the drawing, a filtrate stream is fed through line 10 into Concentration unit 11. Nitric acid, monocarboxylic acids and other volatile components which co-distill with water are removed through line 12. A concentrate solution of reduced water and nitric acid content is recovered from Concentration unit 11, and passed through line 13 into Esterification unit 14. Methanol is entered into Esterification unit 14 via line 15, and the esterification reaction is conducted at a temperature of 70° C. for a period of about 15 minutes to form methyl esters of $C_4$–$C_6$ carboxylic acids.

The esterification reaction medium is withdrawn continuously from Esterification unit 14 through line 16 and introduced into Extraction unit 17. An organic solvent (e.g., benzene) is fed countercurrently into Extraction unit 17 by means of line 18. The extraction cycle is conducted at a temperature of 70° C. for a contact time of about 5 minutes. The organic solvent phase is recovered from Extraction unit 17 and passed through line 19 into Water Wash unit 20, and there it is contacted countercurrently with water which is fed through line 21 into Water Wash unit 20. The aqueous phase is recovered from Extraction unit 17 and passed through line 23 into Methanol Stripping unit 25. The stripped methanol is recycled to Esterification unit 14 through line 26, and the residual aqueous nitric acid solution and the metal catalyst values contained therein is recycled to the adipic acid production unit through line 27.

The spent water wash stream from Water Wash unit 20 is recycled through line 28 to Extraction unit 17. The washed organic solvent stream is recovered from Water Wash unit 20 and passed through line 29 into Solvent Stripping unit 30. The stripped organic solvent is recycled to Extraction Unit 17 via line 32. A refined mixed dimethyl ester fraction is withdrawn from Solvent Stripping unit 30 through line 33, and charged to Fractional Distillation unit 35. Lines 36, 37, 38 and 39 are employed to isolate the dimethyl succinate, dimethyl glutarate, dimethyl adipate and bottoms fractions, respectively.

The following example is further illustrative of the present invention. The reactants and other specific ingredients are presented as being typical, and various modifications can be derived in view of the foregoing disclosure within the scope of the invention.

EXAMPLE

A filtrate byproduct stream (i.e., waste mother liquor) from an adipic acid manufacturing plant is distilled at subatmospheric pressure to reduce the water and nitric acid contents of the mixture and provide a concentrate solution.

The concentrate solution contains about 70 weight percent of adipic, glutaric and succinic acids. The other main components comprise about 5 weight percent nitric acid, 20 weight percent water, and about 1.0 weight percent copper and 500 ppm of vanadium.

The concentrate solution is maintained in a liquid state at 75° C., and charged to a pressure mix tank, and stirred therein with an approximately equal weight of methanol. Partial esterification is achieved in the mix tank at 75° C. for a period of about 10 minutes.

The esterification medium is fed into an extraction column which is thermostated at 75° C. and which operates at a pressure of about 15 psig. The extraction column contains a 36 inch packed section. The esterification feed is entered continuously into the extraction column at a point six inches below the top of the packed section. Benzene is fed continuously to the bottom of the extraction column, and water is fed continuously to the top of the extraction column. The function of the water is to wash methanol, nitric acid and catalyst values from the benzene phase during the extraction stage. Optionally, the wash procedure can be performed as a subsequent step in a separate unit as illustrated in the drawing.

The volume ratio of benzene to esterification medium in the extraction column is 1:1.5, and the contact time between the two phases is about 5 minutes.

The benzene phase is withdrawn from the top of the extraction column and passed into a short distillation column for the removal of benzene, which is then recycled to the extraction column unit. A mixed dimethyl ester fraction is recovered from the short distillation column and, optionally, subjected to fractional distillation to yield dimethyl adipate, dimethyl glutarate and dimethyl succinate as high purity compounds.

The aqueous wash phase which is withdrawn from the bottom of the Extraction column is concentrated in a methanol stripping unit. The methanol is recycled to the mix tank esterification unit, and the residual aqueous nitric acid solution containing the copper and vanadium catalyst values is recycled to the cyclohexanone/cyclohexanol oxidation unit.

As an alternative procedure, the original filtrate byproduct stream is first passed through an ion exchange column to reduce the copper and vanadium to less than 100 ppm. In this case, the subsequently recovered residual aqueous phase from the methanol stripping unit is discarded rather than recycled to the cyclohexanone/cyclohexanol oxidation unit.

What is claimed is:

1. In a process for producing methyl esters of $C_4$–$C_6$ carboxylic acid components contained in an aqueous filtrate, which filtrate is a waste byproduct stream derived from the production of adipic acid by nitric acid oxidation of cyclohexanone/cyclohexanol, the improvement which comprises the steps of (1) concentrating the volume of the aqueous filtrate medium by the partial removal of water and the volatile components which co-distill with water to provide a concentrate solution; (2) admixing the concentrate solution with methanol, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; and (4) separating the immiscible organic solvent phase and aqueous phase.

2. In a method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the organic solvent phase and washing the said phase with water to reduce the content of methanol and residual nitric acid; and (5) recovering the solvent phase which contains dimethyl succinate, dimethyl glutarate and dimethyl adipate components.

3. A process in accordance with claim 2 wherein the starting aqueous filtrate medium contains components comprising succinic acid, glutaric acid, adipic acid, metal catalyst values and nitric acid.

4. A process in accordance with claim 2 wherein the water-immiscible organic solvent in step (3) is selected from aromatic hydrocarbons, halogenated aliphatic hydrocarbons and halogenated aromatic hydrocarbons.

5. A process in accordance with claim 2 wherein the water-immiscible organic solvent in step (3) is benzene.

6. A process in accordance with claim 2 wherein the water-immiscible solvent in step (3) is employed in a quantity between about 0.5–2 volumes per volume of esterification medium.

7. In a method for producing dimethyl esters of $C_4$–$C_6$ carboxylic acid components contained in an aqueous filtrate, which filtrate is a waste byproduct stream derived from a process for producing adipic acid by nitric acid oxidation of cyclohexanone/cyclohexanol, the improvement which comprises the steps of (1) concentrating the volume of the aqueous filtrate medium by the removal of water and the volatile components which co-distill with water to provide a concentrate solution which has a water content between about 5–30 weight percent and a nitric acid content between about 1–6 weight percent, based on total solution weight; (2) admixing the concentrate solution with between about 20–60 weight percent methanol, based on total solution weight, and heating the solution at a temperature between about 60° C.–90° C. to form methyl esters of the $C_4$–$C_6$ carboxylic acid components; (3) extracting the methyl ester components by contacting the esterification medium with a water-immiscible organic solvent at a temperature between about 40° C.–90° C.; (4) separating the immiscible organic solvent phase and aqueous phase; (5) fractionally distilling the organic solvent phase to recover a refined mixed dimethyl ester fraction; and (6) concentrating the aqueous phase by distillation to provide a residual aqueous solution containing nitric acid and metal catalyst values.

8. A process in accordance with claim 7 wherein the mixed dimethyl ester fraction recovered in step (5) comprises dimethyl succinate, dimethyl glutarate and dimethyl adipate.

9. A process in accordance with claim 7 wherein the dimethyl esters in step (5) are recovered as individual components.

10. A process in accordance with claim 7 wherein additionally monomethyl esters of dicarboxylic acids are recovered in step (5), and recycled to step (2) of the process.

11. A process in accordance with claim 10 wherein the recycled esters are monomethyl esters of succinic acid, glutaric acid and adipic acid.

12. A process in accordance with claim 7 wherein the organic solvent is recovered in step (5) and step (6) and recycled to step (2) of the process.

* * * * *